US012383205B2

(12) United States Patent
Olivatto Fioravanti et al.

(10) Patent No.: US 12,383,205 B2
(45) Date of Patent: Aug. 12, 2025

(54) METHOD FOR ESTIMATING PHYSIOLOGICAL EVENTS FROM PHYSIOLOGICAL SIGNALS, A NON-TRANSITORY COMPUTER-READABLE MEDIUM, AND, AN APPARATUS

(71) Applicant: SAMSUNG ELETRÔNICA DA AMAZÔNIA LTDA., São Paulo (BR)

(72) Inventors: Vanessa Brischi Olivatto Fioravanti, Campinas (BR); Paula Gabrielly Rodrigues, Campinas (BR); Rafael Goncalves De Lima, Campinas (BR); Otavio Augusto Bizetto Penatti, Campinas (BR)

(73) Assignee: SAMSUNG ELETRÔNICA DA AMAZÔNIA LTDA., Campinas (BR)

( * ) Notice: Subject to any disclaimer, the term of this patent is extended or adjusted under 35 U.S.C. 154(b) by 646 days.

(21) Appl. No.: 17/684,818

(22) Filed: Mar. 2, 2022

(65) Prior Publication Data
US 2023/0200741 A1 Jun. 29, 2023

(30) Foreign Application Priority Data
Dec. 27, 2021 (BR) ...................... 10 2021 026473-0

(51) Int. Cl.
*A61B 5/00* (2006.01)
*A61B 5/0205* (2006.01)
(Continued)

(52) U.S. Cl.
CPC .......... *A61B 5/7267* (2013.01); *A61B 5/0205* (2013.01); *A61B 5/02416* (2013.01);
(Continued)

(58) Field of Classification Search
USPC ....................................................... 702/190
See application file for complete search history.

(56) References Cited

U.S. PATENT DOCUMENTS 10,750,960 B2  8/2020 Miao et al.
10,939,875 B2  3/2021 Fischer et al.
(Continued)

FOREIGN PATENT DOCUMENTS

EP   1 354 553 A1   10/2003

OTHER PUBLICATIONS

Paul van Gent et al., "HeartPy: A novel heart rate algorithm for the analysis of noisy signals", Transportation Research Part F, 2019.
(Continued)

*Primary Examiner* — Paul D Lee
(74) *Attorney, Agent, or Firm* — STAAS & HALSEY LLP (57) ABSTRACT

Accurate peak detection in physiological signals is fundamental for several tasks related to health monitoring. A method for fine-tuning candidate peak positions and detecting peaks of interest in signals is provided. The fine-tuning method addresses the problem of low signal resolution and reduces the error with respect to the gold-standard reference signal usually collected at higher sampling frequencies. Obtaining accurate peak positions without modifying the sampling frequency is essential in the context of wearable devices, which often present limited computational resources and storage. Furthermore, the method enables selection of the peaks of interest by classifying their tuned positions according to a set of features extracted from morphological characteristics of the signal. The present pipeline is illustrated through inter-beat interval (IBI) estimation from wrist-PPG signals collected from smartwatches. The method may also be suited to the refinement and detection of different fiducial points, including peaks and valleys of interest.

25 Claims, 4 Drawing Sheets

(51) Int. Cl.
*A61B 5/024* (2006.01)
*A61B 5/0285* (2006.01)
*A61B 5/352* (2021.01)
*A61B 5/369* (2021.01)

(52) U.S. Cl.
CPC ........ *A61B 5/02438* (2013.01); *A61B 5/0285* (2013.01); *A61B 5/352* (2021.01); *A61B 5/369* (2021.01); *A61B 5/681* (2013.01); *A61B 5/7207* (2013.01); *A61B 5/7221* (2013.01); *A61B 5/7225* (2013.01)

(56) References Cited

U.S. PATENT DOCUMENTS

| | | | |
|---|---|---|---|
| 2020/0178821 A1 | 6/2020 | Wu et al. | |
| 2020/0196898 A1* | 6/2020 | Hajimolahoseini | A61B 5/36 |
| 2021/0369209 A1* | 12/2021 | Braun | A61B 5/02416 |
| 2022/0015713 A1* | 1/2022 | Kaminsky | G06N 20/00 |

OTHER PUBLICATIONS

Bing Nan Li et al., "On an automatic delineator for arterial blood pressure waveforms", Biomedical Signal Processing and Control, 2009.

Eli Billauer, peakdet: Peak detection using MATLAB (non-derivative local extremum, maximum, minimum), Tech Blog, Jan. 2009.

* cited by examiner

METHOD FOR ESTIMATING PHYSIOLOGICAL EVENTS FROM PHYSIOLOGICAL SIGNALS, A NON-TRANSITORY COMPUTER-READABLE MEDIUM, AND, AN APPARATUS

CROSS-REFERENCE TO RELATED APPLICATION(S)

This application is based on and claims priority under 35 U.S.C. § 119 to Brazilian Patent Application No. BR 10 2021 026473-0, filed on Dec. 27, 2021, in the Brazilian Intellectual Property Office, the disclosure of which is incorporated by reference herein in its entirety.

FIELD OF THE DISCLOSURE

The present invention relates to the field of healthcare technology, health monitoring and monitoring fitness activities through wearable devices. More specifically, the present invention relates to a method for optimizing the detection of peaks or valleys of interest in the context of physiological digital signals, also providing fine-tuning of these initially detected positions. The proposed method includes receiving a digital signal representing a physiological process measured from the sensors of wearable devices and extracting health information from physiological events that might be detected from certain signal peak morphologies.

In particular, the present invention is illustrated, in a non-limitative manner, by means of the heartbeat detection problem from Photoplethysmogram (PPG) signals, which are optical signals used to detect volumetric changes in blood in peripheral circulation. One of the main challenges of properly detecting such a peak event from the PPG is that this signal is in general subject to different noise sources. In addition, a typical PPG waveform has two distinct characteristic peaks, which represent the systole and the diastole phase of the cardiac cycle. In this case, the signal peaks may represent undesired components depending on many factors, such as the sensor location, the environmental light intensity and the presence of motion that results in sensor displacement. PPG signals may also include high frequency noise, potentially causing several undesired peaks (false positive events), as well as low frequency noise, potentially causing several failures in detecting peaks of interest (false negative events) due to low signal amplitude variation.

DESCRIPTION OF RELATED ART

Heart rhythm abnormality, hereinafter referred to as arrhythmias, is a condition that occurs when the electrical impulses in the heart do not work properly, causing the heart to beat irregularly, either too slowly or too fast. The electrocardiogram (ECG) is a signal that records the electrical activity of the heart and it has been typically used as a reliable cardiac monitoring technique to identify arrhythmias. Nevertheless, for its effective operation, several electrodes must be attached to the body and this may narrow the user's mobility.

On the other hand, the PPG signal is a relatively simples and low-cost optical measurement method that is often used for heart-rate monitoring purposes. The PPG is a noninvasive technology that uses a light source and a photodetector at the surface of the skin in order to measure the volumetric variations of blood circulation in the blood vessels.

The R peak is a characteristic point in the ECG signal. It is used to measure the time interval between each heartbeat. The time duration between each R peak is referred to as the RR-interval. Since the RR-interval extracted from the ECG signal is the gold-standard method for this type of measurement, it is frequently used for classifying several cardiac arrhythmias, such as the atrial fibrillation (AF). The estimation of the heartbeat intervals relies on the detection of the systolic peaks in a certain heartbeat signal. Therefore, it is also possible to estimate the same RR-intervals through the PPG signal by detecting and, eventually, fine-tuning the systolic peaks positions of each systole event. The RR-interval estimated from PPG is often referred to as the inter-beat interval (IBI).

If accurately determined, the IBI should perfectly match the corresponding RR-intervals obtained from a synchronized ECG signal. Recent advancements in PPG signal processing have stimulated the development of wearable wrist-worn heart-rate sensors, which have enjoyed widespread acceptance worldwide. This technology is increasingly demanding attention from healthcare and technology professionals around the world.

The accurate estimation of IBI signal is an important step for several tasks involving health monitoring, such as the early diagnosis of cardiovascular diseases and the detection of stress or hypertension. In addition, it is possible to estimate the Heart-Rate Variability (HRV), which is also an important feature for the computation of sleep stages and post-exercise recovery, to name a few.

However, the variation signal of the blood volume delivered by these PPG devices may often be highly contaminated by motion artifacts and other additional noise sources. Although a preprocessing stage may include different types of filtering techniques for noise reduction, this may result in unwanted smoothing of the signal and the loss of physiologically meaningful aspects thereof. Thus, it is not advisable to only rely on preprocessing stages for removing all the false (undesired) peaks. The filtering-based preprocessing blocks may also add unwanted information.

The PPG signal resolution is given by the inverse of its sampling frequency. Particularly, the sampling frequency of the PPG signals from wearable devices is low and in general not appropriate for accurate IBI estimations aiming at heart-rate variability (HRV) estimation and AF detection algorithms.

In the state of the art, there are several documents related to peak or valley detection and signal processing in biological and/or health data.

For instance, a method for peak detection on biological cyclic signals using a supervised approach is presented in "Optimized Real Peak Detection in Cyclic Biological Data Signals" (U.S. Ser. No. 10/939,875B2), by Fujitsu limited. The disclosed method includes optimizing a linear score function from a set of known peak positions and the derived features. The method also includes a filtering step for signal denoising. The proposed scoring function combines and weights fourteen features. These features are derived only within the time range defined according to the underlying physiological source signal, from which all the candidate peaks will be assessed and eventually selected as the peak of interest. Note that at least a single peak of interest is expected to lie on the defined time range. Due to that, this may be a critical aspect with respect to generalization ability of the method proposed in U.S. Ser. No. 10/939,875B2. For instance, when the source signal represents the physiological properties from the human heart rate, this time range must be set to 2000 ms, considering the heart rate as 30 beats per minute. On the other hand, considering two hundred beats per minute, this interval must be set to 300 ms. Note that other physiological events may have different ranges. No further details about the range selection module are presented in U.S. Ser. No. 10/939,875B2. For heartbeat interval estimation, we assume this module relies on a specific heart rate estimator for tuning the appropriate time range, wherein the algorithm would look for the systolic peak. We also remark that, even considering the same supervised learning framework for peak detection, we found no mentions on specific fine-tuning methods of the peak positions with respect to the known ones and used as reference. This is also an import factor for differentiating the method proposed hereinafter from the one presented in U.S. Ser. No. 10/939,875B2.

The features proposed in U.S. Ser. No. 10/939,875B2 include the minimum and maximum sample values within the time range, the peak amplitude, the peak timestamp, the amplitudes and the timestamps of the preceding and following valleys, the slope between the peak of the left valley, the slope between the peak of the right valley, the difference between the samples highest and the lowest amplitude, the maximum slope and the timestamp of the expected peak location. During the training phase, the coefficients of the linear scoring function are optimized using a linear machine learning technique, such as a linear regression method, support vector machine, etc. On deployment phase, after the score is computed among all the candidate peaks in the selected time range, only the peak with the highest score is identified as the one of interest.

Similar to the disclosure of U.S. Ser. No. 10/939,875B2, the present method employs certain features for identifying the peaks of interest. However, in the present approach these features are not based neither on the absolute amplitudes nor on the absolute timestamps. In the present invention, the features are computed from the relative difference between adjacent peaks and valleys with respect to the candidate peak under assessment. Since different amplitude scales and significantly distinct rhythms can be observed on digital physiological signals, an approach based on relative characteristics (from the difference between two points), are possibly a more robust and flexible alternative for similar applications. Furthermore, they represent a more generalist and viable alternative in the analysis of various types of biological signals Another important point is that the present method is capable of fine-tuning and identifying peaks or valleys of interest without depending on the choice of a specific time range. This is an important benefit of the present method, considering that the choice of the optimal time range may depend on very specific conditions related to the collection of digital physiological signals, which may vary over time. Moreover, instead of selecting a single peak or valley with the highest score within a certain time range previously established, the present method uses the features to train a specific non-linear machine learning algorithm based on the known peaks or valleys positions in the reference signal. Another remarkable aspect is that the present method is perfectly suited for real-time applications and requires low computational resources in terms of memory and processing power. Thus, the proposed method is a convenient alternative also in the context of mobile or wearable devices.

The method proposed in "Apparatus and method for detecting heartbeat using PPG" (EP1354553A1), by Samsung Electronics Co. Ltd., presents another peak detection approach for specifically detecting the heartbeats from PPG signals in the presence of motion artifacts. This method relies on detecting candidate heartbeat sequences from the PPG signal after calculating an expected mean inter-beat interval through a signal processing technique. Such technique is based on the wavelet transformation and the autocorrelation function. The preprocessing module is composed of a resampling step, particularly useful whenever the sampling frequency is higher than needed, followed by the first hard threshold process, in which the resampled signal is compared to a predetermined base level, and finally a second threshold process applied to the coefficients from the wavelet decomposition of the signal after the first hard threshold stage. In the first hard threshold process, the samples that are lower than the threshold level are replaced by zero, whereas the samples that are greater than the threshold level are kept unchanged. The second hard threshold process substitutes zero values for the wavelet components having smaller amplitudes than a predetermine value and extracts only the components having greater amplitude among the detail transform coefficients. As a result, the high frequency noise is mostly removed. After these steps, a clipping and a convolutional module are added to adjust the signal for the computation of the mean heart rate.

In a similar way to EP1354553A1, the present invention uses the same mechanism for extraction of the candidate peaks based on the zero-crossing points from the approximate first derivative signal. However, in EP1354553A1, the systolic peaks are selected from the candidate peaks only in the neighborhood of the expected mean IBI. The mean IBI is computed through the autocorrelation function. The autocorrelation function presents a non-periodical signal component associated to the noise (random noise) converging to zero, while a periodical signal component with a large amplitude value at the time corresponding to its own period. Scores are assigned to each of the peaks selected from the original candidate peaks, and the optimum heartbeat sequence is updated based on the highest achieved scores. Finally, the selected sequence is used to update the mean heart rate estimation.

Since the main goal in EP1354553A1 is in fact the estimation of the mean heart rate, an accurate peak detection method is not the most important aspect expected to be achieved from this invention. We can notice that much of the precision on determining the systolic peak positions may be lost due to the adopted preprocessing methods. These methods result in a very approximated version of the PPG signal. Also, another limiting factor of the accuracy obtained is the own assumption of an average IBI based on which the following candidate peaks will be selected. The method of the present invention, on the other hand, is mostly focused on a high degree of precision with respect to the peak/valley position estimations, which are afterward assessed through the set of known peak/valley positions derived from the reference signal. Although our method is particularly convenient for applications that require greater precision in determining the positions of each resulting peak and intervals of interest, it could also be adapted to the same context of average heart rate estimation from the instantaneous IBI values.

Still in the context of wearable devices, the method described in "Passive Arrhythmias Detection Based on Photoplethysmogram (PPG) Inter-Beat Intervals and Morphology" (U.S. Ser. No. 10/750,960B2), by Samsung Electronics Co. Ltd., proposes an approach for classifying cardiac arrhythmias using PPG signal and the corresponding IBI estimates. In a similar way to the present invention, the pipeline in U.S. Ser. No. 10/750,960B2 includes slicing the signal into short segments and discarding those segments that are identified as poor quality (as these segments are likely to result in unreliable IBI estimations) and whose waveform morphologies are significantly affected by motion artifacts and other sources of noise.

In U.S. Ser. No. 10/750,960B2 the IBI estimates are taken as either the time gap between adjacent PPG pulse onset positions or the time gap between adjacent systolic peak positions. These peaks or onset positions are selected based on an adaptive threshold method, which is adjusted from the heart rate estimates derived from the ECG signal. In the present invention, the candidate peaks are initially detected from the derivative of the preprocessed signal and the IBI is estimated using the systolic peaks adjusted and selected by a machine learning classification algorithm. Before feature extraction, the peak positions are fine-tuned using a customized method that learns the optimized parameters from a set of ECG known peak position. Although the focus of the proposed method is not ultimately the classification of cardiac arrhythmias, the proposed approach may be extended to that specific purpose.

In addition, the main advantage of the proposed invention with respect to the method proposed in U.S. Ser. No. 10/750,960B2 is that the peak detection and fine-tuning methods are both data-driven algorithms, which do not rely on empirical thresholds and rule-based modes to identify the peaks of interest (in this particular case, the systolic peaks). Furthermore, the methods proposed in the present invention could also be perfectly adapted to the purpose of pulse onset detection using the same ECG known R-peak positions in order to learn the parameters of each employed model: the one for fine-tuning the peak positions and the one for peak classification.

Another method for detecting cardiac arrhythmia is provided in "Method And Device For Detecting Cardiac Arrhythmia Based On Photoplethysmographic Signal" (US20200178821A1). This method includes filtering out motion artifacts and other noise sources in the PPG signal, obtaining the heart rate according to the spectrum and determining whether cardiac arrhythmias are present in the signal. The method for detecting cardiac arrhythmia is based on the filtered PPG signal segments and the corresponding estimated heart rate. The IBI estimate is obtained from the following equation:

$$D_{min} = \frac{(\text{Sampling rate})}{(\text{Estimated heart rate})} - \alpha \times (\text{Sampling rate})$$

where $\alpha$ is a coefficient between 0 and 1. From $D_{min}$, several derived features are extracted in order to feed a prediction model that determines whether cardiac arrhythmia is present. A few examples of such features are: the standard deviation of $D_{min}$; the root mean square of successive differences of $D_{min}$; and the entropy of $D_{min}$.

Note that the present invention relies neither on spectral parameters, nor on the heart rate estimation from the preprocessed PPG signal. Instead, the proposed method relies on the straightforward estimation of the systolic peaks found in the time domain.

In prior-art document "On an automatic delineator for arterial blood pressure waveforms", by authors Li B N, Dong M C and Vai M I, it is proposed an adaptive threshold method based on the first derivative signal. The signal is divided in block of 5 s. The candidate peaks are extracted from the zero-crossing points of the first derivative signal. The threshold is adapted according to the mean of amplitudes in a 2 s window and only the candidate peaks with larger amplitudes than the calculated threshold are kept.

In document "A robust method for pulse peak determination in a digital volume pulse waveform with a wandering baseline", by authors Jang D G, Farooq U, Park S H, Hahn M., a slope sum function with an adaptive threshold method is proposed. The main purpose of the slope sum function is to enhance the upslope of the PPG pulse. All the local maximum points are extracted from this function. The threshold is constantly updated to 70% of the median value between the last peaks and only the data samples with amplitude larger than this threshold are kept.

In "Peak detection using MATLAB. Detect Peaks in a Vector", by authors Billauer, E., Haifa, Israel, a data sample is considered a peak of interest whether it has the local maximal value and is preceded by another peak with amplitude difference larger than the preset threshold. The threshold is manually tuned to be one half of the average peak to peak amplitude in the dataset.

In "Systolic peak detection in acceleration photoplethysmograms measured from emergency responders in tropical conditions", by authors Elgendi M, Norton I, Brearley M, Abbott D, Schuurmans D., they propose a method that relies on the signal squaring, which emphasizes the large amplitude differences generally observed around the peak of interest, suppressing the small differences arising around unwanted peaks. Blocks of interest are generated using two event-related moving averages that demarcate the peak of interest. The samples with the largest amplitude values in each extracted block ultimately become the peak of interest identified by the method.

In "A novel heart rate algorithm for the analysis of noisy signals", by authors van Gent P, Farah H, van Nes N, van Arem B. Heart, they propose an adaptive threshold method to accommodate for morphology and amplitude variation in particular to the PPG typical waveforms, followed by outlier detection and rejection. To identify true systolic peaks, a threshold is updated from the calculated moving average in a window of length 0.75 s on both sides of each signal sample.

In "Stress Detection With Single PPG Sensor by Orchestrating Multiple Denoising and Peak-Detecting Methods", by authors Heo S, Kwon S, Lee J., they propose an ensemble-based peak-detection method, which relies on five peak-detection methods of the state of the art. The final peak position is determined through the decision by majority vote applied to the results of the five techniques aggregated by the method in question.

In fact, most of these methods employ adaptive threshold functions in order to decide whether to keep or discard the originally detected peaks. Because these approaches are reliant on certain threshold updating rules and many tunable parameters, usually, they do not generalize well when applied to much different datasets than those used to introduce the results of the technique. Furthermore, they do not achieve good performance, especially when data distribution may vary, for instance, depending on demographic characteristics, or the sensors employed in collecting the signals.

On the other hand, the approach proposed in the present invention is based on a tailor-made fine-tuning mechanism of the original peak or valley positions, as a way of mitigating low sampling frequency of the signals, a flexible feature extraction system, which converts the peak or valley detection problem into the task of classifying the peaks or valleys of interest in the signal.

Thus, the proposed fine-tuning method is a relevant contribution to the state of the art since the problem of low resolution in physiological signals has never been treated in a supervised way, as proposed herein. Furthermore, the peak or valley detection problem in physiological signals is not usually treated as a classification problem, although it is possible to find other applications in different fields of study, where the use of other feature extraction methods and other classification techniques are also employed for the same task. However, as will become apparent in the present description, the peak or valley detection method of the present invention has also novel aspects in comparison with those based on other Machine Learning techniques and previously reported in the prior-art.

SUMMARY OF THE INVENTION

The present invention is composed by techniques for fine-tuning and detecting the peaks or valleys of interest on physiological signals. The proposed methods may be easily adapted to different signals, datasets and applications. Also, such method require low computational cost while keeping higher levels of accuracy when compared to the prior-art methods. The proposed methods may be easily adapted to different types of signals as well as to different contexts and applications.

More specifically, the present invention refers to a method for estimating physiological events from digital physiological signals received from one or more devices, comprising the steps of: detecting candidate peaks or valleys on the one or more physiological signal, fine-tuning the positions of the detected candidate peaks or valleys using a first machine learning, ML, algorithm trained in a supervised manner to minimize errors relative to a reference signal, learning the best interpolation strategy from the neighboring samples to the point of interest; extracting features from the fine-tuned candidate peaks or valleys, and classifying, using the extracted features and a second ML algorithm trained in a supervised manner, the fine-tuned candidate peaks or valleys to identify peaks or valleys of interest; and estimating one or more physiological events using the previously identified peaks or valleys of interest.

Furthermore, the present invention additionally refers to a non-transitory computer-readable medium comprising computer-readable instructions that, when executed by a processor, cause the processor to perform the method of the present invention.

In addition, the invention refers to an apparatus, a processor and a non-transitory computer-readable medium, wherein the non-transitory computer-readable medium comprises computer-readable instructions that, when executed by a processor, cause the processor to perform the method as defined in the present invention.

BRIEF DESCRIPTION OF THE DRAWINGS

The invention is explained in greater detail below on the basis of figures. Shown therein are.

DETAILED DESCRIPTION OF THE INVENTION

As mentioned before, previous methods of peak or valley detection in the art usually rely on certain threshold functions and empirically determined rule-based strategies in order to decide whether to keep or discard the peaks or valleys from the signal of interest. Nevertheless, these methods are usually not easily tunable, especially on datasets containing different signal morphologies.

The systolic peak detection problem may be used as a toy example for illustrating such scenario, in which the goal is estimating heartbeat intervals using PPG dataset recordings from different groups of users with and without any type of cardiac arrhythmia. Because the signal morphology of the users with arrhythmia is different than that of the healthy ones, threshold functions and rule-based approaches are not easily calibrated due to the differences in static distributions of these signals. Therefore, a new method for peak or valley detection and fine-tuning the peak or valley positions is proposed herein, so that higher accuracy and reliability throughout a context-invariant solution, that may be extended to different application domains and datasets can be achieved.

The identification of peaks or valleys that obey certain waveform morphologies is a fundamental aspect to detect events in many physiological and biological processes such as those represented by signals from electrocardiograms (ECG), electroencephalograms (EEG), sympathetic neuronal activity and pulse oximetry, to name a few. For example, to determine several health biomarkers and to detect many health conditions, such as the aforementioned cardiac arrhythmias, it is common to rely on peak or valley detection algorithms designed to select and, preferably, refine positions thereof in the corresponding signal domain.

Often, it is necessary to detect peaks or valleys in real time using the signals collected from wearable devices. Since the raw signals may include several sources of noise and other interference mechanisms, this task may be challenging due to the sensor characteristics and types, sensor position on user's body, and most importantly, due to the user's activity levels and intensities. Current approaches tend to be complicated, specific to particular domains, and dependent on several tunable parameters.

Figure 1:
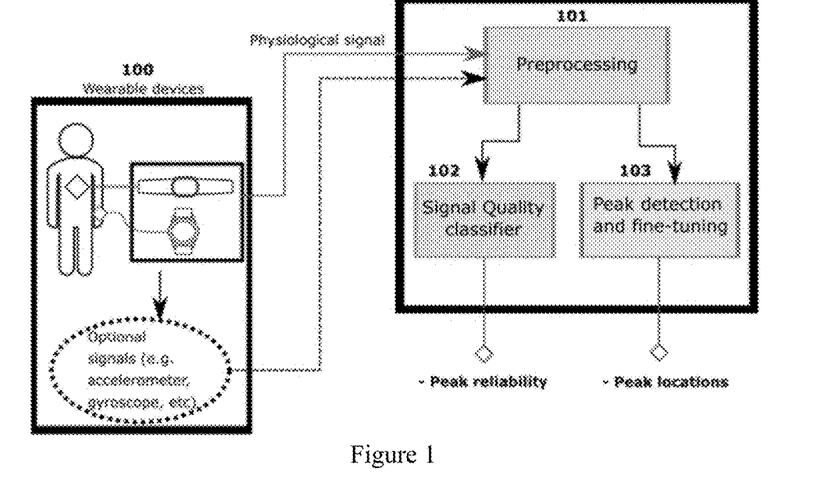
FIG. 1 presents the complete pipeline for peak or valley detection and fine-tuning of physiological signals, according to an embodiment of the present invention.

FIG. 1 illustrates a general block diagram for implementing the methods of the present invention in applications in which accurate peak detection in physiological signals collected from sensors in wearable devices is desired. The signals 100 from the wearable devices may include physiological signals, such as the volumetric changes in blood in peripheral circulation, collected through PPG sensors, as well as other optional signals to improve the preprocessing, in step 101. These optional signals may be included in the preprocessing pipeline in order to facilitate noise reduction and the motion artifact removal techniques. Examples of such signals may be accelerometer sensor data and gyroscope sensor data. Note that, although the preprocessing step 101 may include different types of filtering techniques for noise reduction, this may result in unwanted smoothing and the loss of physiologically meaningful aspects of the signal. Therefore, one cannot conveniently rely solely on such preprocessing step 101 for removing all the false (undesired) peaks. In certain situations, these filtering-based preprocessing steps 101 may also add unwanted contents to the signal.

The strategy proposed herein to mitigate this problem is to use a novel method for peak or valley detection enhanced by a fine-tuning method in block 103, preferably including signal quality classifier 102 to determine the reliability of the detected peak or valley after the signal pre-processing stage in 101. Blocks 102 and 103 make the proposed pipeline more robust and replicable not only to situations involving the IBI estimation from PPG signals, but also in other contexts requiring reliable estimates of peak or valley positions of interest.

Several methods from the state-of-the-art employ threshold functions in peak detection and fine-tuning steps in order to decide whether to keep or discard the peaks detected after a certain preprocessing step. However, these threshold algorithms usually rely on several tunable parameters that are not easily adaptable to datasets containing different signal morphologies. Therefore, a new method for fine-tuning and peak detection is proposed herein so that one can achieve results with improved robustness and precision by means of a context-invariant solution, which may be generalized for multiple physiological signals.

In order to more clearly illustrate these methods, a pipeline for estimating the heartbeat intervals from PPG recordings collected from healthy volunteers and volunteers with cardiac arrhythmias is shown in the present description. In this non-limitative example case, it will become apparent that these methods are in fact quite adaptable to different signal morphologies such as that from volunteers with and without cardiac arrhythmias. In addition, it will be shown that the proposed solution does not rely on complex implementations nor on several tunable parameters.

To overcome the aforementioned limitations of the state-of-the-art, the present invention proposes a new algorithm for handling peak or valley detection and fine-tuning of specific peak or valley positions on physiological signals that are hard to identify on physiological signals. It is presented a new approach for fine-tuning the candidate peak or valley positions, according to the peak or valley annotations from a ground-truth signal and a peak or valley classification method that is designed to be generic and easily automated. The proposed approach employs a learning-based fitting model for obtaining the optimal polynomial coefficients around the original peak or valley positions and a classification model that identifies the peaks or valleys of interest based on a set of proposed features. In particular, the present solution may focus on the detection of systolic peaks from PPG recordings in order to estimate the intervals between successive heart beats (IBI). Note that this specific context and the application itself is only intended to illustrate the proposed methods that will be introduced in the next sections and is in no way should be understood as a limitation of the invention.

The fine-tuning method is a tailor-made optimization approach for refining the peak or valley positions initially detected in the preprocessed PPG signal. The objective of this optimization is to learn the weights that represent the importance of the interpolation error in each sample used in the process that occurs in the neighborhood of the originally detected point of interest. It requires a ground-truth signal from which the true expected peak or valley positions of interest can be extracted. Thus, one can optimize the choice of certain fitting parameters during the algorithm's training phase and then obtain well-adjusted peak or valley positions with minimum mean squared error with respect to the reference peak or valley positions.

In addition, the proposed peak or valley detection method relies on a set of handcrafted features that feed a classification algorithm. This algorithm is trained to identify the peaks or valleys of interest (e.g. systolic peaks), as well as the undesired ones (e.g. diastolic peaks, remaining noise spikes, etc.).

The present invention does not rely on the conventional approaches found in the art, especially those reported in the context of physiological signal processing tasks, which are based either on adaptive thresholds or rule-based methods. Furthermore, the present invention also has novel aspects in comparison with the existing approaches based on Machine Learning techniques for peak detection. In order to mitigate the aforementioned limiting aspects from the prior-art solutions, the present invention proposes supervised learning methods for two tasks: the peak detection and the fine-tuning. The proposed fine-tuning method is a substantial contribution, since the problem of low resolution in physiological signals has never been approached in a supervised way.

It is worth mentioning, though, that despite its adaptability and good performance when compared to other solutions in the art, the proposed algorithms are not computationally complex and do not require memory or processing resources that are not normally viable in the context of wearable/mobile devices.

Best Mode (1st Embodiment)

The proposed IBI estimation pipeline includes three different layers and each of them plays either a supportive role or the main role involving the peak detection, the fine-tuning and the IBI estimation. The preprocessing layer 202, 203, illustrated in FIG. 2 aims at emphasizing the systolic peaks, as well as removing or attenuating noisy spikes/peaks. Since motion artifacts and other noise sources may present a serious challenge for obtaining clear and reliable PPG signals for IBI estimation, it is therefore necessary to include robust preprocessing methods in order to preserve relevant signal information and discarding the undesired components from the noise sources.

Since IBI estimation from optical signals is highly sensitive to noise, it is of particular interest to perform accurate IBI estimation during resting conditions. For this reason, the dataset was collected in a laboratory environment where the data acquisition protocol consisted of rest. The acquisition lasted approximately one hour for each volunteer. The ECG data was collected using an FDA-approved ECG patch. The ECG signal quality and the systolic peaks were manually annotated by clinicians in order to produce a gold standard for the supervised learning of the models. These annotations 210 are indicated in the block diagram of FIG. 2, which will be further discussed later, and will be employed only for the training phase of the proposed algorithms of peak detection and fine-tuning. The PPG signal quality 211 was annotated according to the beat morphologies observed in the signal. These annotations will only be required for the training phase of the employed method of PPG signal quality classification. The PPG and the accelerometer data were collected with a sampling rate of 100 Hz, using a Samsung Watch Active 2 and the ECG signal at 500 Hz using electrodes. These signals were decimated to 25 Hz in order to approximate the restricted processing capacity usually observed on smartwatch processors.

Figure 2:
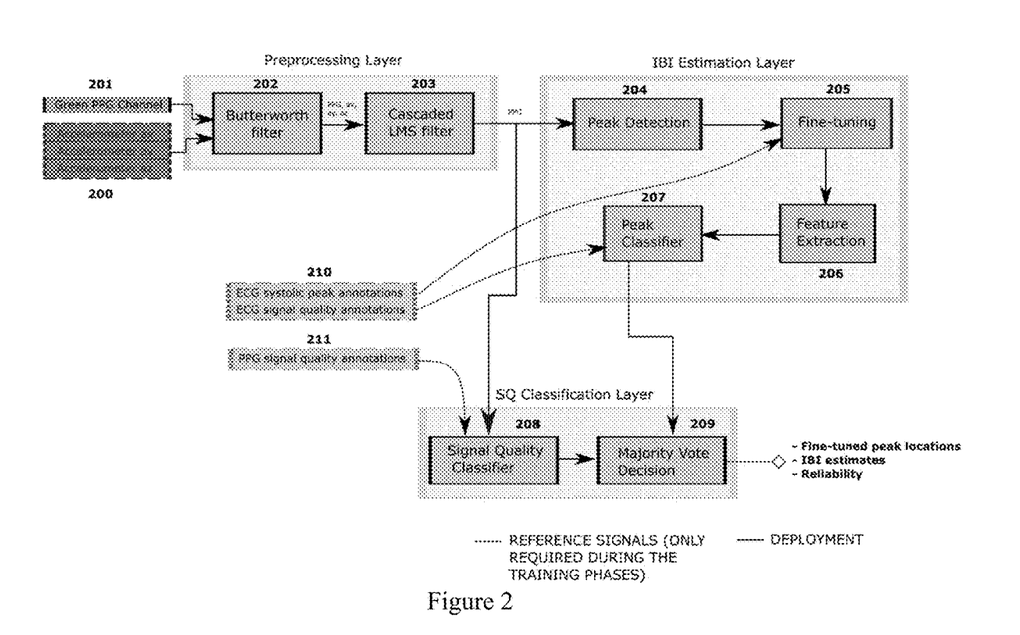
FIG. 2 shows an overview of an exemplary pipeline for IBI estimation using PPG and accelerometer signals in accordance with the present invention, according to an embodiment of the present invention.

In the present pipeline, a simple and efficient preprocessing approach is used, which is based on two consecutive steps. In the first preprocessing block 202, we use a bandpass filter that is initially applied to the raw green PPG channel in order to suppress low frequency oscillations, as well as those high frequencies that do not contribute to emphasize the systolic peaks at the frequency range of interest. Particularly, in the present preferred embodiment of the invention, an Infinite Impulse Response (IIR) Butterworth filter of second-order with passband frequencies designed at 0.8 Hz and 4.5 Hz is used.

The second preprocessing block 203 consists of an adaptive noise cancellation (ANC) technique using feedback connection of the least-mean-square (LMS) adaptive filters. The ANC is used to remove unwanted motion artifacts, which may cause sensor displacement and signal distortions. The purpose of the ANC is to yield an anti-wave signal whose magnitude is exactly similar to that of the unwanted noise (captured from accelerometer signals) and whose phase is exactly opposite to that. The cascaded adaptive filtering approach shown in the preferred embodiment of FIG. 2 uses three channels from accelerometer data in order to reduce the effects of motion artifacts. Note that both preprocessing blocks' algorithms may be replaced by other methods and techniques that might present a better fit to a particular environment. It is worth mentioning that said replacement in principle would not bring any significant changes in the overall format of the proposed peak detection and fine-tuning methods and in fact.

Because the IBI estimation from optical signals is generally not reliable in the presence of intense movement and other signal interferences, the proposed method is able to detect the events of poor signal quality and discard the unreliable estimates based on the preprocessed PPG wave morphology. Therefore, the risk of incorrect IBI estimations is considerably minimized. To that end, at the Signal Quality (SQ) classification layer 208,209, it is proposed the use of a shallow 1D-CNN (Convolutional Neural Network) architecture in the Signal Quality Classifier 208 block. This block classifies poor quality and good quality PPG segments. For the supervised training stage, an automatic method may be used to create the labels to each segment from manual notes made by experts.

For training purpose of the classifier, we first use a sliding window method to create segments of 75 samples, with 70 overlapping samples. This large sample overlap is an effective choice to allow a more balanced decision regarding the quality of each peak detected in the IBI estimation layer. Since each sample of the PPG signal is encompassed at 15 different segments, the final classification at the sample level may be taken as the majority vote decision 209 block, between the classification results of each segment. In practice, this leads to higher levels of accuracy of the classifier at the sample level than using a single non-overlapping segment to determine the quality of a certain sample marked as a systolic peak.

In the second step, the signal in each segment is normalized via a min-max normalization within the interval [0,1]. Finally, each segment is labelled according to a stated threshold, w. If the human-based annotation fraction of good quality PPG samples 211 that lies within a certain segment is higher than the fraction stated in w, then the window is labelled as good quality. The peaks that eventually lie on this segment are voted as reliable, referring to the first segment where they are contained. Due to the sliding window scheme, the results of another fourteen segments will be part of the decision about each of the peaks detected by the system. On the other hand, if the annotated fraction of good quality PPG samples 211 within this segment is lower than the fraction stated in w, then the segment is labelled as poor quality. The peaks that eventually lie on this segment are at least voted as unreliable (out of a total of 15 votes that will form part of their respective final reviews). The set of preprocessed PPG segments along with the corresponding generated labels feed the 1-D CNN model at the training stage.

During the training phase of the 1D CNN model, w is set as w=0.8. During the deployment phase, the network's probabilistic threshold is set as p=0.8. This means that only the segments predicted with high confidence, i.e., p>0.8 are in fact classified as good quality. This parameter may regulate the relationship between the algorithm coverage and accuracy of IBI estimates. With the chosen value p=0.8 suitable coverage levels were reached and at the same time the precision of the estimates was maintained.

Note that the short description of this functional layer is intended to illustrate a single possible approach to solve the PPG signal quality classification problem in the context of accurate IBI estimation. However, it is noted that other approaches may be followed in SQ task without any significant disadvantages to the proposed peak detection and fine-tuning methods. The IBI estimation layer will be further detailed next.

IBI Estimation Layer

At the IBI estimation layer, our framework is based on three steps, which are the focus of the present invention. These steps are sequentially performed in the following order:

(I) First, the positions of the candidate PPG peaks and the signal valleys are obtained in the peak detection 204 block. This block is able to detect such events using the results from sign changes around zero-crossing points of the approximated first derivative signal.

(II) A tailor-made interpolation method for fine-tuning 205 the peak positions in a supervised manner that makes use of the synchronized ECG reference systolic peak positions. This method provides significant improvements especially in terms of the performance metrics (e.g. mean absolute error or root mean square error) that consider the difference between the peak positions resulting from the evaluated physiological signal and the peak positions indicated by an expert from the reference physiological signal.

(III) A feature extraction 206 block and a classification model 207 for systolic peak detection. These blocks are responsible for extracting features from the fine-tuned peak positions, as well as classifying these candidate peaks as either a True (T) systolic peak or a False (F) systolic peak (a diastolic peak or a noise peak). Note that, during the training phase of both models, we have only used the features and the labels extracted within the good quality segments from the PPG and the ECG signals. This was made in order to ensure that the model's learning is carried out from informative and reliable content.

Detecting the Candidate Peaks

After the signal preprocessing methods 202, 203, the motion artifacts and other interferences are expected to be considerably reduced and thus the resulting signal is left with substantially less noisy spikes/peaks. Therefore, it becomes reasonable to start selecting the candidate systolic peaks on the preprocessed signal by simply detecting all the time locations where the remaining peaks lie. Additionally, in order to classify the candidate peaks as either a True or a False systolic peak, it is also necessary to find the time locations of the PPG signal valleys. The valley positions will be useful for extracting the features with respect to each candidate peak in the feature extraction block 206.

Figure 3A:
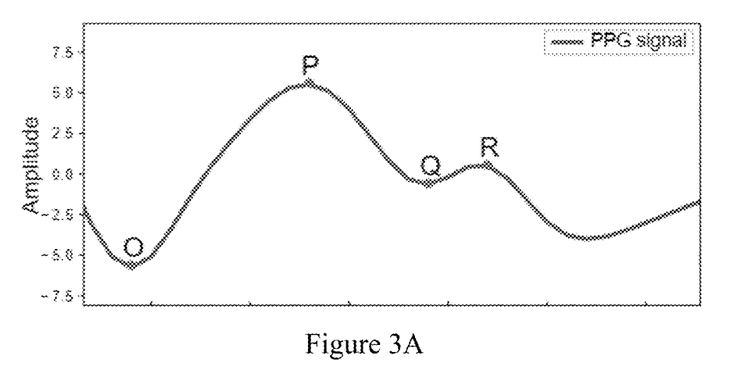
FIGS. 3A and 3B illustrates the main coordinates of a PPG peak (O: valley; P: Systolic Peak; Q: Dicrotic Notch; R: Diastolic Peak), according to an embodiment of the present invention.

For detecting each candidate peak, the derivative of the preprocessed PPG signal may be approximated by taking the difference between adjacent samples. A typical preprocessed PPG signal is shown in FIG. 3A. Considering a discrete-time preprocessed PPG signal x[t], the i-th candidate systolic peak point, $p_i$, is identified using its adjacent samples, i.e., if $x[p_i-1]<x[p_i]>x[p_i+1]$, then $p_i$ is the index of a candidate peak. In other words, from a downward trend around the zero-crossing points of the approximated first derivative signal, such as in data points P and R illustrated in FIG. 3B, we can track all the candidate systolic peak. This approach is hereinafter referred to as the three-point sliding window method.

Figure 3B:
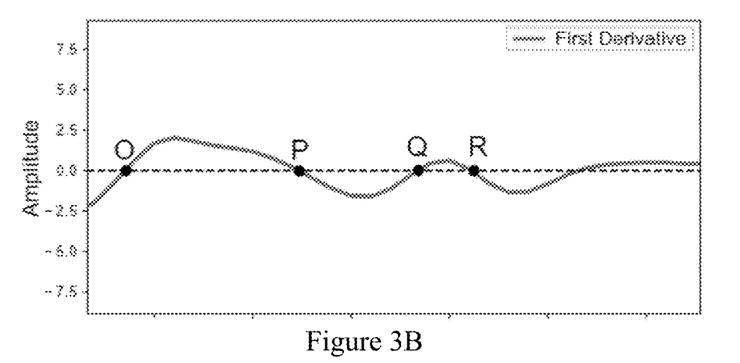

Similarly, if the derivative signal has an upward trend at the zero-crossing point, a valley such as those data points O and Q illustrated in FIG. 3B can be tracked. In other words, the sample index of the k-th valley point, $v_k$, is also identified using adjacent sample differences, i.e. $x[v_k-1]>x[v_k]<x[v_k+1]$.

After detecting all the candidate peaks and all the valleys on the preprocessed signal, the next step consists in fine-tuning the peak positions using the method of the present invention. This method is intended to optimize the choice of the weights associated to the error parcels of each sample used for fitting a quadratic polynomial in the neighborhood of the peak under assessment. It will become apparent that optimizing these weights will naturally lead to minimizing the peak position error with respect to the expected peak position from the reference physiological signal.

Fine-Tuning PPG Systolic Peaks

The PPG signal resolution is given by the inverse of the sampling frequency. In particular, the sampling frequency of the PPG signals processed in our proposed framework is $f_s=25$ Hz, although higher or slightly lower frequencies may be used as well. This corresponds to a sampling period $t_s=40$ ms, which is usually not enough for accurate IBI estimations aiming, for example, at Atrial Fibrillation (AF) detection. The low sampling frequency is a common constraint shared between several wearable devices such as smartwatches. However, this may be mitigated by a tailor-made interpolation method for fine-tuning the candidate PPG peak positions, by using weights learned through the proposed optimization for the interpolation of PPG samples in the neighborhood of the originally detected peak. These weights are optimized once from the positions of the reference peaks, taken from the synchronized ECG signal.

For finding the most appropriate peak position based on the positions indicated by a reference physiological signal, a second order polynomial $\phi_i(t)$ is adopted for interpolating the samples in the neighborhood of each peak position, i, from the physiological signal used for evaluation. In particular, the ECG signal is used as the reference physiological signal and the PPG signal as the physiological signal used for evaluation of the proposed method for IBI estimation.

The polynomial coefficients may be obtained from the sample values in the neighborhood $j \in \{-2,-1,0,1,2\}$, such that $\phi_i(t_{ji})=a_i t_{ji}^2 + b_i t_{ji} + c_i \approx y_{ji}$, where $y_{ji}$ is the amplitude of the signal at the j-th neighbor point from the i-th peak. Without losing generality, five neighbor samples are used in the proposed pipeline. Note that j=0 indicates the peak position itself. The present method is inspired by the Weighted Least Squares (WLS) regression method, which is an example of the broader class of generalized least squares estimators. In particular, the goal is optimizing the choice of the weights $w_j$ associated to each fitting error parcel $e_{ji}$ of a quadratic polynomial in the neighborhood of the i-th peak, i.e.:

$$e_i = \Sigma_{j=-2}^{j=2} w_j e_{ji}^2$$

$$e_{ji} = a_i t_{ji}^2 + b_i t_{ji} + c_i - y_{ji}.$$

To that end, we learn the weights w based on the neighbor PPG signal samples $y_{ji}$ for minimizing the error $e_i$ with respect to the reference peak position, $p_i$, obtained from corresponding peak of interest annotations in the ECG signal. Note that, the learning process includes the optimization of a single set of weights $w=[w_{-2}, w_{-1}, w_0, w_1, w_2]^T \in \mathbb{R}^5$ to all data points included in the training dataset, as well as the polynomial coefficients $\{a_i, b_i, c_i\}$ calculated for each detected peak, i. The optimization problem is defined as:

$$w^*, \delta^*, a_i^*, b_i^*, c_i^* = \operatorname{argmin}_{w,\beta,a_i,b_i,c_i} \sum_{i \in P} \left(-\frac{b_i}{2a_i} + \delta - p_i\right)^2$$

$$\text{subject to } [a_i \; b_i \; c_i] = (X_i^T W X_i)^{-1} X_i^T W y_i$$

$$W_k > 0, k \in \{-2, -1, 0, 1, 2\}$$

$$\sum_{k=-2}^{2} w_k = 1$$

where $W=\text{diag}(w_{-2}, w_{-1}, w_0, w_1, w_2)$ is a diagonal matrix with the weights of each sample used for interpolation, $y_i \in \mathbb{R}^5$ is a vector containing the PPG amplitudes of the five data points in the neighborhood of the i-th peak, including the peak amplitude as well, i.e., $y_i=[y_{-2i}, y_{-1i}, y_{0i}, y_{1i}, y_{2i}]^T$, and $X_i$ is a matrix defined as $$X_i = \begin{bmatrix} t_{-2i}^2 & t_{-2i} & 1 \\ t_{-1i}^2 & t_{-1i} & 1 \\ t_{0i}^2 & t_{0i} & 1 \\ t_{1i}^2 & t_{1i} & 1 \\ t_{2i}^2 & t_{2i} & 1 \end{bmatrix}$$

In particular, setting the number of samples used for interpolation to five, the set $\{t_{-2i}, t_{-1i}, t_{0i}, t_{1i}, t_{2i}\}$ indicates the time coordinates of the data points with relative positions $\{-2, -1, 0, 1, 2\}$ in the neighborhood of the i-th peak. Note that the system of equations $X_i[a_i, b_i, c_i]^T = y_i$ would be overdetermined and occasionally would have no solution. The effect of including the weight matrix W to this system of equations is to induce the solution of the least-squares problem that minimizes the error between the adjusted peak positions $$\text{i.e., } -\frac{b_i}{2a_i} + \delta$$

and the reference peak positions, $p_i$. With this, it is expected that the interpolation mechanism can be more precise and easily generalizable to the context of different applications.

The parameter $\delta$ is an additional decision variable included in the learning process. Its main role is to ensure that more flexible conditions are obtained for the adjustment imposed by the interpolation. Note that, the right-hand side of the equation with the coefficients of the polynomial $\phi_i(t_{ji})$ is itself the analytical solution of the weighted least squares problem defined as $$\min_{a_i, b_i, c_i} \Sigma_{j=-2}^{j=2} w_j e_{ji}^2.$$

For every peak position i and without being less general, we may set $t_{0i}=0$ and store its original value in $t_{0i}^*$ such that the remaining neighbor data point time instant positions $t_{ji}$ would be shifted backward and forward by one or two sampling periods of the signal with respect to the origin position occupied by the peak. As the sampling frequency is held constant, $X_i$ is in fact a constant matrix X. For obtaining the optimized parameters $w^*$, $\delta^*$, $a_i^*$, $b_i^*$, $c_i^*$, a differential evolution method is applied to solve the optimization problem earlier presented. The data required for the training phase of this algorithm are the set of candidate systolic peaks and the corresponding set of five neighbor samples, as well as the reference ECG signal peaks $p_i$ from the manual annotation from experts.

In summary, the set of weights w that properly balance the interpolation error parcels at each sample used in the process of adjusting the position and amplitude of the i-th candidate peak. The utmost goal of the proposed optimization is to minimize the error between the fine-tuned PPG systolic peak position and the corresponding ECG systolic peak. Note that, once these weights are optimized it is possible to find, in real time, the optimal coefficients of the polynomial of each detected peak with low computational cost.

On the deployment stage, once w and δ are optimized, the solution of the equation with the coefficients of the polynomial $\phi_i(t_{ji})$ is a simple vector-matrix multiplication since all the terms before $y_i$ may be precomputed only once and beforehand. The fine-tuned peak position is then calculated as:

$$\tau = -\frac{b_i}{2a_i} + \delta + t_{0i}^*$$

where $t_{0i}^*$ is the original time instant from the i-th peak.

None of the conventional approaches investigated in the prior-art have mentioned a method of determining the fine-tuned peak position by optimizing a certain set of parameters in order to better fit the peak positions to the corresponding positions in the reference signal. The methods investigated in the prior-art are blind approaches from the perspective of the target reference peak positions $p_i$. Due to the optimization phase in the proposed fine-tuning method, a significant improvement is achieved in terms of the mean absolute error (MAE) and the root mean squared error (RMSE) calculated with respect to the obtained fine-tuned peak positions and those from the reference. Furthermore, the proposed method does not add great complexity in the deployment stage, since most operations with high computational cost are done only during the parameter optimization stage, which is done only once and in advance (during the training phase).

Extracting Features and Classifying the Candidate Peaks

Figure 4:
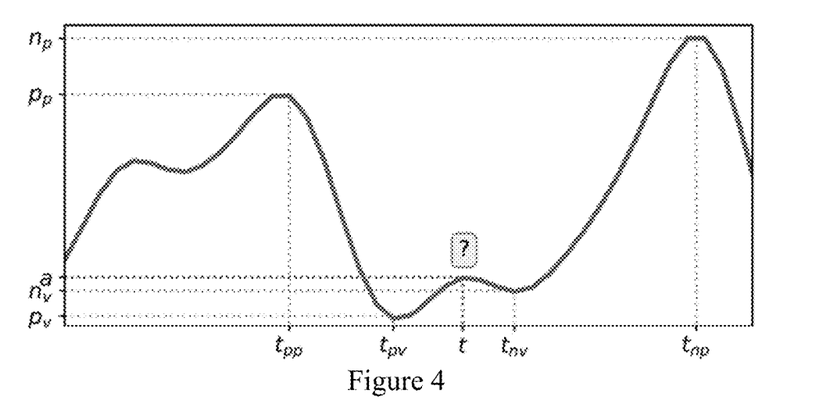
FIG. 4 illustrates the first derivative signal across the PPG wave, according to an embodiment of the present invention.

To decide whether the fine-tuned candidate peaks are actually systolic peaks, the MLP model was trained to learn binary labels associated to either true (T) or false (F) peaks using nine extracted features. These features include the relative amplitudes and the relative time gaps between the candidate peak under assessment, its previous and its following neighbor peaks and valleys. The vector containing these features is given by $$m = \begin{bmatrix} a_{pp} \\ a_{pv} \\ a_{nv} \\ a_{np} \\ a \\ d_{pp} \\ d_{pv} \\ d_{nv} \\ d_{np} \end{bmatrix} = \begin{bmatrix} a-p_p \\ a-p_v \\ a-n_v \\ a-n_p \\ a \\ t-t_{pp} \\ t-t_{pv} \\ t-t_{nv} \\ t-t_{np} \end{bmatrix},$$

where the relative amplitude features refer to the amplitude difference between the peak under assessment and the amplitude from either the previous detected peak, $a_{pp}=a-p_p$, or the following peak, $a_{np}=a-n_p$. The same reasoning is followed with respect to the neighbor valleys, i.e., $a_{pv}=a-p_v$ and $a_{nv}=a-n_v$. The amplitude coordinates from the neighbor peaks and the valleys are shown in FIG. 4. The relative distance features represent the time gaps between the peak under assessment and the neighbor peaks and valleys, i.e., $d_{pp}=t-t_{pp}$, $d_{pv}=t-t_{pv}$, $d_{nv}=t-t_{nv}$ and $d_{np}=t-t_{np}$. The time coordinates from the neighbor peaks and the valleys are shown in FIG. 4. The scalar a refers to the amplitude of the peak under assessment itself.

Figure 5:
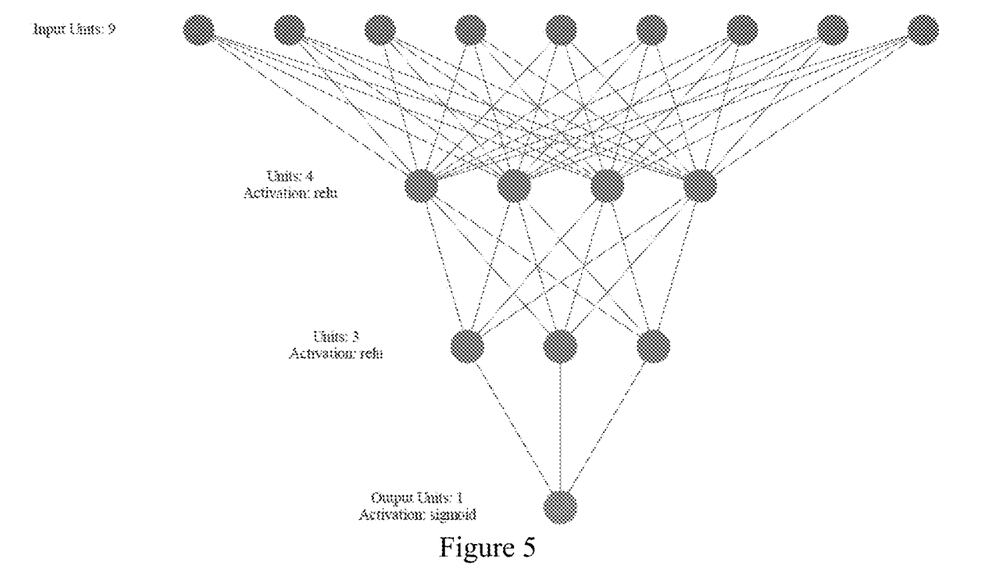
FIG. 5 illustrates the Multi-Layer Perceptron (MLP) model used as peak or valley classifier, according to an embodiment of the present invention.

The MLP model consists of four layers: the input layer, two additional hidden layers, and the output layer. The artificial neural network scheme is illustrated in FIG. 5. The input nodes correspond to the ensemble of relative amplitudes and distance features described previously. The hidden layers contain four and three neurons, respectively. The non-linearity of the neurons from these layers are produced with the Rectified Linear Unit (ReLU) activation function. Because the problem is stated in terms of a binary classification problem, there is a single output neuron that uses the sigmoid activation function. The output value is between 0 and 1 to represent the probability of predicting a value for the class T, of true systolic peaks. Therefore, the typical probabilistic threshold p=0.5 is used for transforming the values below this threshold to F or otherwise to T.

To train the MLP model, the stochastic gradient descent (SGD) and the adaptive data momentum (ADAM) optimization algorithms were examined in terms of the classification accuracy achieved on the validation dataset. The training and the validation datasets comprise a series of tuned candidate peaks, whose features are extracted from peaks and valleys in the neighborhood and the corresponding peak labels, either T or F. These labels are obtained after matching the candidate peaks and the corresponding systolic ECG peaks. The ECG reference systolic peak and a candidate systolic PPG peak are matched if they are in the window of up to 150 ms from each other. In this case, the candidate peak is labelled as T. Otherwise, if the candidate peak is not matched with any ECG peak within the stated guard interval it is labelled as F. All the candidate peaks employed throughout the training stage were only taken from the intersection of good quality segments from PPG and ECG signals.

The techniques described in this step allow an accurate detection of peaks in physiological signals using data-driven techniques. In the method according to the present invention, the systolic peak detection task is treated through a set of features derived from previous and future events with respect to a certain tuned candidate peak in the preprocessed physiological signal. A classifier algorithm is then proposed to identify only the peaks of interest according to the input features. In addition, the proposed framework may also provide accurate results while running on embedded devices such as smartphones and smartwatches.

Alternatives (2nd/3rd Embodiments)

The present invention could also be extended to a broader range of applications related to different physiological signals, used for monitoring many other health events. Furthermore, with small adaptations, the disclosed method could be also employed for onset detection of a certain event and other particular points of interest. Hereinafter, we show how our method may be utilized on two additional use-cases.

Pulse Onset Detection in CBFV Waveforms

Assessment of cerebrovascular function is required in the diagnosis of several neurological conditions. Transcranial Doppler (TCD) ultrasound is used to measure the cerebral blood flow velocity (CBFV), which may be useful for assessing cerebral hemodynamics and for evaluating specific brain functions. TCD has established clinical indications for several brain disorders such as acute ischemic stroke and stenosed or occluded intracranial vessels. The CBFV may be also useful as a tool for noninvasive intracranial pressure monitoring and the assessment of mild traumatic brain injury.

The CBFV waveform analysis often relies on the typical signal morphology and certain metrics derived from its characteristic points. As a matter of fact, this analysis heavily depends on two aspects involving CBFV processing: reliable pulse onset and peak detections. However, accurate detections in CBFV waveforms also include several challenges:

(I) the attenuation of the signal by the skull, resulting in low signal to noise ratio;
(II) the signal quality, which is highly influenced by the operator's skills on locating the acoustic window and which may vary widely from patient to patient;
(III) the motion artifacts, which may significantly interfere and distort the original CBFV morphology;
(IV) the wide range of waveform morphologies that can occur in CBFV signals. Due to that, it is often difficult to rely on threshold-based mechanism of detection as its adaptation rules may likely fail.

Despite these difficulties, TCD remains a valuable diagnostic tool that is inexpensive, noninvasive, fast, and portable. The ECG signal may serve as a ground-truth signal for locating the onset points from CBFV signals, which may be reliably determined from the R peak positions of the QRS complex. These peak annotations from the ECG signals may be more conveniently obtained from an expert professional that in general finds less haziness in analyzing the ECG signal than in the corresponding CBFV signal. Note that, locating the QRS peak from the ECG signal is a mature biomedical signal processing technique that may facilitate the processing of pulsatile cardiovascular signals such as the CBFV.

Figure 6:
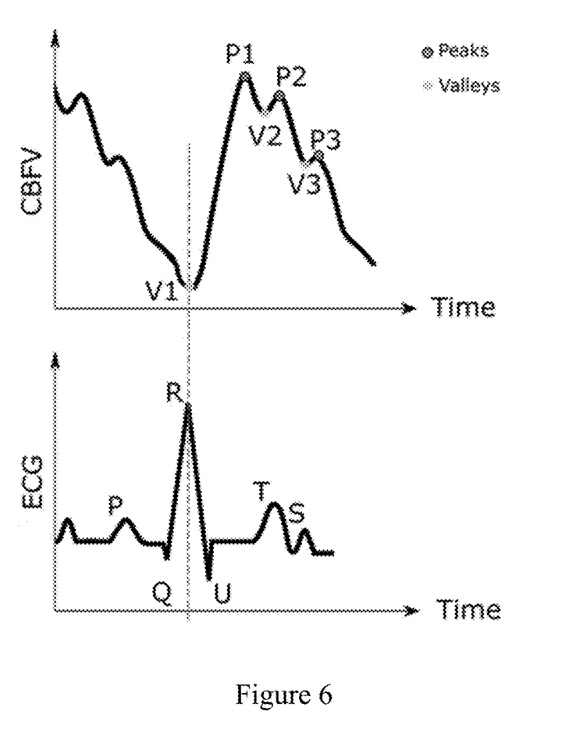
FIG. 6 illustrates a typical cerebral blood flow velocity (CBFV) waveform with six landmarks and the synchronized ECG signal, according to an embodiment of the present invention.

As the CBFV often requires the ECG synchronized recordings as a complementary signal to support on the medical analysis of CBFV, the method according to the present invention could be extended for refining and detecting the onset positions of interest directly from the CBFV. This could be a viable and data-driven alternative for learning how to determine the CBFV characteristic points directly from this signal and based on the annotations performed on the ECG signal. On deployment phase, the ECG signals would no longer be required for supporting the CBFV analysis. With a gold-standard source indicating systolic peak positions that also delimit the beginning of the CGFV pulse, the proposed method according to the present invention would be able to optimize the fitting parameters and the coefficients of the interpolation polynomial in the neighborhood of the candidate onset positions of the CBFV signal, as well as training the proposed classifier to detect the onset positions of interest from the CBFV signal itself.

FIG. 6 illustrates a typical CBFV waveform, with six landmarks. We can see that the CBFV waveform morphology has three representative peaks indicated as P1, P2 and P3 and three representative valleys, V1, V2 and V3. There might be at least one alternative for detecting the onset point, V1, using the disclosed fine-tuning and peak detection methods. For instance, we may use the R peak position from the gold-standard ECG signal in order to optimize the parameters and the coefficients used for the polynomial fitting in the neighborhood of each candidate onset positions from CBFV signal. Similarly, an onset classifier could be fed with analogous features with respect to the onset positions instead of the candidate peak positions, as used for the application involving IBI estimation from PPG signals. As a result, we could provide an automatic and reliable method for detecting the onset positions directly from the CBFV waveforms. The ECG recordings and the expert annotations would not be required after the training phase with the appropriate datasets.

Automated Identification of Epileptiform Discharges from EEG Recordings

Electroencephalography (EEG) is an important tool in the diagnosis of patients with suspected epilepsy. Interictal epileptiform discharges (EDs) are the biomarkers of epilepsy and seizure risk. Improved patient care and the possibility of home monitoring increased the number of EEG records. This represents a huge demand for experts on interpreting these signals. Unfortunately, there is a scarcity of such experts qualified to interpret the EEG results. In addition, the agreement of experts on identifying epileptiform EEG discharges is usually low and there is an increasing need for methods of automated EEG analysis. In particular, these methods are expected to provide an objective and standardized analysis. The present invention's methods for fine-tuning peak positions and detecting ED peaks could potentially lead to valuable algorithms in such a domain.

In 2019, a deep learning-based detection algorithm for EDs was validated and compared to scorings made by experts, with remarkable results. In 2020, it was described a semi-supervised method of deep learning-based detection of ED requiring low amount of labeled EEC data for training. Detected EDs are automatically grouped into clusters, consisting of the same type of EDs, for rapid visual inspection. The diagnostic gold standard was derived from the video-EEG recordings of the patients' habitual events. The disclosed invention could contribute as a novel machine learning-based ED detection approach for assisting neurophysiologist in rapid assessment of EEG recordings.

Figure 7:
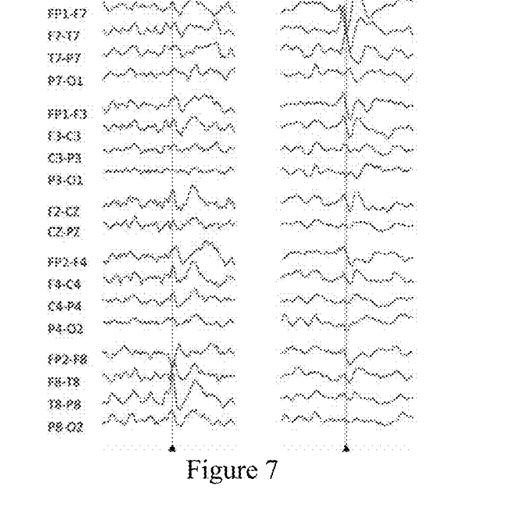
FIG. 7 illustrates the EEG signals and the epileptiform discharges (ED) peaks, according to an embodiment of the present invention.

First, the candidate ED peaks and the valley positions can be extracted from each preprocessed EEG channel. Assuming the ED peak annotations from each channel are not independent, a single E) peak annotation must hold for all the analyzed EEG channels. As a result, the fine-tuning method could be trained to enhance the ED peak positions of each channel based on the time location indicated by the expert. Finally, the features from each enhanced candidate peak could be extracted based on the previous and the following neighbor peak and valley positions under analysis. With the features extracted from each candidate peak on each EEG channel and the expert annotations, we could train an appropriate classification algorithm to recognize the patterns of the ED peaks.

Hardware Implementation

The example embodiments described herein may be implemented using hardware, software or any combination thereof and may be implemented in one or more computer systems or other processing systems. Additionally, one or more of the steps described in the example embodiments herein may be implemented, at least in part, by machines. Examples of machines that may be useful for performing the operations of the example embodiments herein include general purpose digital computers, specially-programmed computers, desktop computers, server computers, client computers, portable computers, mobile communication devices, tablets, and/or similar devices. Preferably, the present method is tailored for use in wearable devices such as smartwatches and/or patches.

For instance, one illustrative example system for performing the operations of the embodiments herein may include one or more components, such as one or more microprocessors, for performing the arithmetic and/or logical operations required for program execution, and storage media, such as one or more disk drives or memory cards (e.g., flash memory) for program and data storage, and a random-access memory, for temporary data and program instruction storage.

The system may also include software resident on a storage media (e.g., a disk drive or memory card), which, when executed, directs the microprocessor(s) in performing transmission and reception functions. The software may run on an operating system stored on the storage media, such as, for example, UNIX or Windows (e.g., NT, XP, Vista), Linux, and the like, and can adhere to various protocols such as the Ethernet, ATM, TCP/IP protocols and/or other connection or connectionless protocols.

As is well known in the art, microprocessors can run different operating systems, and can contain different types of software, each type being devoted to a different function, such as handling and managing data/information from a particular source, or transforming data/information from one format into another format. The embodiments described herein are not to be construed as being limited for use with any particular type of server computer, and that any other suitable type of device for facilitating the exchange and storage of information may be employed instead.

Software embodiments of the illustrative example embodiments presented herein may be provided as a computer program product, or software, that may include an article of manufacture on a machine-accessible or non-transitory computer-readable medium (also referred to as "machine-readable medium") having instructions. The instructions on the machine accessible or machine-readable medium may be used to program a computer system or other electronic device. The machine-readable medium may include, but is not limited to, floppy diskettes, optical disks, CD-ROMs, and magneto-optical disks or other type of media/machine-readable medium suitable for storing or transmitting electronic instructions.

Therefore, the present invention also relates to a non-transitory computer readable storage medium method for estimating physiological events from physiological signals received from one or more devices. The storage medium comprising computer readable instructions that, when performed by the processor, cause the processor to perform the method steps previously described in this disclosure.

The techniques described herein are not limited to any particular software configuration. They may be applicable in any computing or processing environment. The terms "machine-accessible medium", "machine-readable medium" and "computer-readable medium" used herein shall include any non-transitory medium that is capable of storing, encoding, or transmitting a sequence of instructions for execution by the machine (e.g., a CPU or other type of processing device) and that cause the machine to perform any one of the methods described herein. Furthermore, it is common in the art to speak of software, in one form or another (e.g., program, procedure, process, application, module, unit, logic, and so on) as taking an action or causing a result. Such expressions are merely a shorthand way of stating that the execution of the software by a processing system causes the processor to perform an action to produce a result.

Technical Effect

In the present section it is first introduced the data collection, the protocol aspects, and the data splitting approach adopted to the performed experiments. Next, the pipeline is evaluated in terms of the improvements obtained from the proposed fine-tuning method when compared to the Ordinary Least Squares (OLS), which is usually employed for similar tasks. These improvements are shown in terms of the reduction achieved in the RMSE calculated for the IBI estimates. Finally, the accuracy of the proposed peak classification method, as well as the error between the IBI estimates and the RR interval from the reference annotations performed on the corresponding ECG signals are also demonstrated.

As previously mentioned, the dataset was collected in a resting environment settled inside a laboratory of data acquisition. These acquisitions last approximately one hour for each volunteer. The ECG data was collected using an FDA-approved ECG patch. Clinicians manually annotated the ECG signal quality and the systolic peaks in order to produce reliable references. In total, the protocol acquisitions resulted in 35.2 hours of synchronized PPG, ECG and accelerometer data from 46 volunteers. There are three study groups: group 1 includes 9 volunteers with permanent AF; group 2 includes 16 subjects with normal sinus rhythm; and group 3 consists of 21 volunteers with other non-specified arrhythmias. The majority of the volunteers are older than 60 years, with a mean age of 66 years old and a median of 70 years old.

The dataset was split into training, validation, and test sets. The data from 64% of the volunteers in each assessment group was used for training the MLP model for peak classification, for optimizing the weights from the peak fine-tuning method, and for training the PPG signal quality classification model (1D-CNN). For validation, the data from 16% of the volunteers in each assessment group was selected. The data from the remaining 20% of the volunteers in each group was used for testing the proposed algorithms. Table 1 summarizes the number of volunteers in each group.

TABLE 1

Dataset splitting and assessment groups.

|  | Train/Validation | Test |
|---|---|---|
| Group 1: Permanent AF | 7 | 2 |
| Group 2: Normal Sinus Rhythm | 13 | 3 |
| Group 3: Other Arrhythmias | 17 | 4 |
| TOTAL | 37 | 9 |

Fine-Tuning Peak Positions

The improvements achieved in terms of the proposed fine-tuning method are shown in Table 2, where it is shown the RMSE values of IBI calculated from the PPG systolic peaks fine-tuned according to both the OLS and the proposed fine-tuning method with respect to the corresponding ECG systolic peaks. Group 1 includes the volunteers with permanent AF, group 2 includes the volunteers with normal sinus rhythm, and group 3 includes those with other non-specified arrhythmias.

The OLS is a linear least squares method for estimating the unknown parameters in a linear regression model. In particular, it can be used for estimating the quadratic polynomial coefficients using the following equation:

$$[a_i b_i c_i] = (X_i^T X_i)^{-1} X_i^T y_i$$

where $y_i = [y_{-1i} \ y_{0i} \ y_{1i}]^T$ and $X_i$ is the matrix defined as:

$$X_i = \begin{bmatrix} t_{-1i}^2 & t_{-1i} & 1 \\ t_{0i}^2 & t_{0i} & 1 \\ t_{1i}^2 & t_{1i} & 1 \end{bmatrix},$$

The elements indicated as $t_{ji}$ are the time coordinates of the two neighbor data points with amplitudes $y_{-1i}$ and $y_{1i}$, as well the original peak position $t_{0i}$. The OLS evaluation is performed with different number of data points (three, five, and seven). The best results obtained from this method were achieved with three points. These results are the ones presented in Table 2. The column "Δ %" represents the percentage variation on RMSE that is achieved with the WLS interpolation algorithm proposed in the present invention. On average, there was a reduction of 10% in the RMSE using our fine-tuning method in relation to the OLS method.

TABLE 2

Evaluation of the proposed fine-tuning method compared to the classical interpolation approach based on the ordinary least squares (OLS).

| | RMSE [ms] | | |
|---|---|---|---|
| Group | Quadratic OLS Interpolation | Proposed WLS Interpolation | Δ % |
| 1 | 20.485 | 18.351 | −10.4% |
| 2 | 14.657 | 12.459 | −15.0% |
| 3 | 19.220 | 18.105 | −5.8% |

Peak Classification

The results achieved on test dataset after ADAM optimization performed to the proposed MLP model are presented in Table 3.

TABLE 3

Confusion matrix of the MLP model for binary classification of the candidate PPG peaks. The label T stands for true systolic peaks and the label F stands for false systolic peaks. Validation accuracy is 97.4%.

| | Predicted | |
|---|---|---|
| | T | F |
| Actual | 99.47% | 0.53% |
| | 10.43% | 89.57% |

IBI Estimation

The IBI estimation performance is evaluated in terms of MAE and RMSE between the estimated IBI and the reference RR interval, extracted from the ECG signals. The peak detection assessment is estimated after matching the synchronized reference ECG systolic peaks and the refined PPG systolic peaks. To compute the number of True Positive peaks, the number of valid matches between the resulting PPG systolic peaks and the reference ECG systolic peaks is counted. The matching is considered valid when the time gap between the PPG peak and the ECG peak is smaller than 150 ms. The unmatched systolic PPG peaks are counted as False Positives, whereas the unmatched ECG systolic peaks are counted as False Negatives.

Table 4 summarizes the results achieved in each group of volunteers with the method of the present invention and with different peak detection algorithms investigated in the prior-art. This experimental validation shows that the present approach outperforms all the threshold based peak detection methods, offering the best compromise between peak detection (f1-score) and fine-tuning (MAE and RMSE). As most of the peak detection algorithms investigated in the literature did not include specific techniques for also refining the peak positions, for the sake of a fair comparison, we adopted the conventional approach, involving a quadratic interpolation via OLS as the post-detection technique applied to those methods.

The peak detection methods were subjected to the same pre-processing and signal-quality classification layers proposed in this pipeline. This ensures that the same reference inputs are shared and therefore, it is possible to better isolate the performance achieved by each method.

TABLE 4

Evaluation of the IBI results calculated for each dataset group using the proposed peak detection and fine-tuning method in comparison to other peak detection and tuning methods via OLS.

| Group | Method | f1-score | MAE | RAISE |
|---|---|---|---|---|
| 1 | Proposed method | 0.959 | 16.445 | 19.522 |
| | HeartPy [11] | 0.934 | 19.330 | 23.220 |
| | Jang et al. [8] | 0.897 | 16.600 | 20.612 |
| | Billauer [9] | 0.957 | 20.535 | 21.908 |
| | Li et al. [7] | 0.934 | 20.505 | 23.631 |
| | Elgendi [10] | 0.916 | 19.245 | 24.042 |
| | Heo et al. [12] | 0.937 | 16.680 | 20.871 |
| 2 | Proposed method | 0.996 | 7.120 | 12.519 |
| | HeartPy [11] | 0.989 | 7.547 | 15.623 |
| | Jang et al. [8] | 0.964 | 7.260 | 15.010 |
| | Billauer [9] | 0.992 | 6.463 | 14.040 |
| | Li et al. [7] | 0.984 | 7.533 | 15.844 |
| | Elgendi [10] | 0.979 | 8.523 | 16.720 |
| | Heo et al. [12] | 0.984 | 7.243 | 15.129 |
| 3 | Proposed method | 0.985 | 13.183 | 19.516 |
| | HeartPy [11] | 0.973 | 16.100 | 22.860 |
| | Jang et al. [8] | 0.907 | 12.975 | 18.921 |
| | Billauer [9] | 0.980 | 14.072 | 20.877 |
| | Li et al. [7] | 0.970 | 16.065 | 22.905 |
| | Elgendi [10] | 0.954 | 15.308 | 21.751 |
| | Heo et al. [12] | 0.956 | 12.590 | 18.719 |

From Table 4, it can be seen that the proposed method was able to achieve accurate systolic peak detections, as observed from higher levels in f1-score in each group of volunteers. Moreover, the fine-tuning algorithm was able to reduce the IBI estimation error due to the refinements on the original peak positions. As a result, the present method achieves low MAE and RMSE even at higher levels of f1-score. Note that although certain competitor methods achieve lower MAE and RMSE levels on certain groups, the corresponding f1-score is much lower than the one achieved with the present method. In practice, this indicates that the other methods achieved lower IBI estimation error simply due to the smaller number of true positive peak detections.

Figure 8:
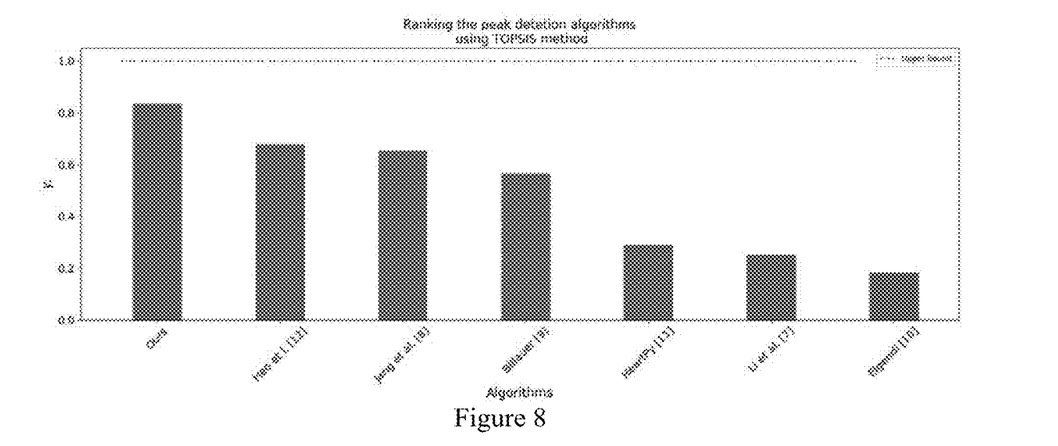
FIG. 8 illustrates the closeness coefficients estimated by Technique for Order of Preference by Similarity to Ideal Solution (TOPSIS), according to an embodiment of the present invention.

The Technique for Order of Preference by Similarity to Ideal Solution (TOPSIS) [23] is one of the most widely used methods of multi-criteria decision-making and algorithm ranking. This method allows a set of alternatives to be evaluated according to a set of criteria. TOPSIS is based on the concept that the chosen alternative should have the shortest distance from the best solution and the longest distance from the worst solution. TOPSIS was used for ranking each algorithm according to nine criteria. Each one of the metrics presented in Table 4, (f1-score, MAE, and RMSE) were independently taken as a criterion for each assessment group. This resulted in a set of 3×3=9 distinct criteria for algorithm evaluation. The weights of each criterion were set to 1/9, due to their uniform relevance to the task under assessment. The relative closeness coefficients $\gamma_i$ are shown in FIG. 8, where a preferable alternative i is the one that poses $\gamma_i$ closer to 1. The results indicate that the present invention, comprising the fine-tuning and the peak detection method, leads the performance rank in the three demographic groups investigated, when compared to the other six alternative solutions from the prior art.

What is claimed is:

1. A method for estimating physiological events from physiological signals received from one or more devices, the method comprising:
   detecting candidate peaks or valleys on the one or more physiological signals,
   fine-tuning positions of the detected candidate peaks or valleys using a first machine learning (ML) algorithm trained in a supervised manner to minimize errors relative to a reference signal;
   extracting features from the fine-tuned candidate peaks or valleys, and
   classifying, using the extracted features and a second ML algorithm trained in a supervised manner, the fine-tuned candidate peaks or valleys to identify peaks or valleys of interest; and
   estimating one or more physiological events using the identified peaks or valleys of interest.

2. The method according to claim 1 further comprising:
   preprocessing the one or more physiological signals to discard unwanted signal components, wherein the preprocessing comprises first and second filtering to suppress unwanted frequencies and motion artifacts in the one or more physiological signals.

3. The method according to claim 2 further comprising:
   determining signal quality of each of a plurality of segments of the preprocessed one or more physiological signals using a third machine learning (ML) algorithm trained in a supervised manner,
   wherein the determining the signal quality further comprises associating each segment with a score and comparing each segment with the score to a probabilistic threshold to discard low quality segments.

4. The method according to claim 3, wherein the supervised training of the third machine learning (ML) algorithm comprises:
   manually annotating photoplethysmogram (PPG) signal quality according to beat morphologies observed in signals from a training dataset;
   applying a sliding window method to create a plurality of segments with overlapping samples to perform quality classification at a sample level in a majority vote decision between classification results of each segment,
   normalizing a signal in each segment via a min-max normalization within the interval [0,1],
   labeling each segment according to a stated threshold, w, wherein:
   provided that the percentage of PPG samples, lying within a sliding window, that are manually annotated as being of good quality is higher than w, then the sliding window is labelled as good quality and the detected peaks that lie on the segment receive at least one vote as reliable, and
   provided the annotated fraction of good quality samples within the segment is lower than w, then the segment is labelled as poor quality and the peaks that lie on the segment receive at least one vote as unreliable.

5. The method according to claim 3, wherein the third ML algorithm is a 1D convolutional neural network (CNN) model.

6. The method according claim 2, wherein
   the first filtering comprises an infinite impulse response, (IIR) Butterworth filter of second-order with passband frequencies designed at 0.8 Hz and 4.5 Hz, and
   the second filtering comprises an adaptive noise cancellation (ANC) technique using a feedback connection of least-mean-square (LMS) adaptive filters.

7. The method according to claim 1, wherein the one or more physiological signals comprise additional signals to facilitate noise reduction and/or motion artifact removal.

8. The method according to claim 7, wherein the additional signals are one or more of accelerometer data and gyroscope data.

9. The method according to claim 1, wherein
   the first ML algorithm is an optimized interpolation algorithm based on weighted least squares regression, and
   the second ML algorithm is a multi-layer perceptron.

10. The method according to claim 1, wherein the minimized errors are at least one of mean absolute error and root mean squared error.

11. The method according to claim 1, wherein the one or more physiological signals are photoplethysmogram (PPG) signals.

12. The method according to claim 11, wherein the estimating physiological events comprises estimating an inter-beat-interval (IBI) to calculate an instantaneous heart-rate of a user using the PPG signals.

13. The method according to claim 1, wherein detecting candidate peaks comprises using results from sign changes around zero-crossing points of an approximated first derivative of preprocessed physiological signals.

14. The method according to claim 1, wherein the algorithms trained in a supervised manner are trained using R peaks in an electrocardiogram (ECG) reference and/or expert made annotations indicating intervals of good and poor quality in photoplethysmogram (PPG) and ECG signals.

15. The method according to claim 1, wherein the fine-tuning further comprises finding the most appropriate peak position by minimizing the error with respect to the peak positions from the reference physiological signal using a second order polynomial $\phi_i(t)$ for interpolating samples in a neighborhood of each peak position i from a physiological signal used for evaluation,
   wherein the coefficients of the polynomial are calculated in real-time, for each candidate peak position, using the weighted least-squares method.

16. The method according to claim 15, wherein, during a training phase of the algorithm, the weights of the second order polynomial $\phi_i(t)$ are only once optimized by solving the following equations:

$$w^*, \delta^*, a_i^*, b_i^*, c_i^* = \operatorname{argmin}_{w,\beta,a_i,b_i,c_i} \sum_{i \in P} \left(-\frac{b_i}{2a_i} + \delta - p_i\right)^2$$

subject to $[a_i \ b_i \ c_i] = (X_i^T W X_i)^{-1} X_i^T W y_i$ $W_k > 0, k \in \{-2, -1, 0, 1, 2\}$ $$\sum_{k=-2}^{2} w_k = 1$$

where $a_i$, $b_i$ and $c_i$ are the polynomial coefficients of $\phi_i(t)$ and may be obtained from the sample values in the neighborhood such that $\phi_i(t_{ji}) = a_i t_{ji} + c_i \approx y_{ij}$, where $y_{ji}$ is an amplitude of the reference physiological signal at the j-th neighbor point from the i-th peak;

$\delta$ is an additional decision variable of the learning process;

$e_i$ is the error and $e_{ji}$ represents the fitting errors parcel;

$p_i$ is the peak position and P is the total of peaks position;

wherein $w = [w_{-2}, w_{-1}, w_0, w_1, w_2]^T \in \mathbb{R}^5$;

$w_j$ represents the weights associated to each fitting error parcel $e_{ji}$ of a quadratic polynomial in the neighborhood of the i-th peak:

$e_i = \Sigma_{j=-2}^{j=2} w_j e_{ji}^2$ $e_{ji} = a_i t_{ji}^2 + b_i t_{ji} + c_i - y_{ji}$ the weight matrix $W = \operatorname{diag}(w_{-2}, w_{-1}, w_0, w_1, w_2)$ is a diagonal matrix with the weights of each data point used for interpolation, $y_i \in \mathbb{R}^5$ is a vector containing the PPG amplitudes of the five data samples in the neighborhood of the i-th peak, including the peak amplitude as well, i.e., $y_i = [y_{-2i}, y_{-1i}, y_{0i}, y_{1i}, y_{2i}]^T$, and $X_i$ is a matrix defined as $$X_i = \begin{bmatrix} t_{-2i}^2 & t_{-2i} & 1 \\ t_{-1i}^2 & t_{-1i} & 1 \\ t_{0i}^2 & t_{0i} & 1 \\ t_{1i}^2 & t_{1i} & 1 \\ t_{2i}^2 & t_{2i} & 1 \end{bmatrix}$$

where $\{t_{-2i}, t_{-1i}, t_{0i}, t_{1i}, t_{2i}\}$ indicate; the time coordinates $\{t_{1i}, t_{2i}\}$ of the two samples prior to a candidate peak position; time coordinates $\{t_{0i}\}$ of the candidate peak itself and time coordinates $\{t_{1i}, t_{2i}\}$ of the two samples that follow the candidate peak position.

17. The method according to claim 15, wherein after the algorithm is trained. the fine-tuned peak position of each candidate peak is calculated as:

$$\tau = -\frac{b_i}{2a_i} + \delta + t_{0i}^*,$$

where $t_{0i}^*$ is the original time instant of the i-th candidate peak and the polynomial coefficients $\{a_i, b_i, c_i\}$ are calculated as:

$[a_i b_i c_i] = (X_i^T W X_i)^{-1} X_i^T W y_i$.

18. The method according to claim 1, wherein the features extracted in the feature extraction form a vector comprising:
amplitude of the candidate peak,
the relative amplitudes between the candidate peak under assessment and a previous neighbor peak and previous valley;
the relative amplitude between the candidate peak under assessment and a following neighbor peak and following valley; and
the relative time gaps between the candidate peak under assessment, a previous and a following neighbor peaks and valleys,
wherein the vector is given by:

$$m = \begin{bmatrix} a_{pp} \\ a_{pv} \\ a_{nv} \\ a_{np} \\ a \\ d_{pp} \\ d_{pv} \\ d_{nv} \\ d_{np} \end{bmatrix} = \begin{bmatrix} a-p_p \\ a-p_v \\ a-n_v \\ a-n_p \\ a \\ t-t_{pp} \\ t-t_{pv} \\ t-t_{nv} \\ t-t_{np} \end{bmatrix},$$

wherein relative amplitude features comprise an amplitude difference between a peak under assessment and amplitude from a previous detected peak, $a_{pp} = a - p_p$, and an amplitude difference between the peak under assessment and amplitude from a following peak, $a_{np} = a - n_p$;

wherein the relative amplitude features further comprise an amplitude difference between the peak under assessment and an amplitude of a previous detected valley, $a_{pv} = a - p_v$, and an amplitude difference between the peak under assessment and an amplitude of a next detected valley, $a_{nv} = a - n_v$;

wherein relative distance features represent the time gaps between the peak under assessment and the neighbor peaks and valleys, that is, $d_{pp} = t - t_{pp}$, $d_{pv} = t - t_{pv}$, $d_{nv} = t - t_{nv}$ and $d_{np} = t - t_{np}$;

wherein the scalar a refers to the amplitude of the candidate peak under assessment.

19. The method according to claim 1, wherein the one or more physiological signals are transcranial doppler (TCD) signals.

20. The method according to claim 19, wherein estimating physiological events comprises estimating the cerebral blood flow velocity (CBFV) of a user using TCD signals.

21. The method according to claim 1, wherein the one or more physiological signals are electroencephalography (EEG) signals.

22. The method according to claim 21, wherein estimating physiological events comprises estimating interictal epileptiform discharges (EDs) using the EEG signals.

23. A non-transitory computer-readable medium storing computer readable instructions that, when executed by a processor, cause the processor to perform the method as defined in claim 1.

24. An apparatus comprising:
a processor; and
a non-transitory computer-readable medium;
wherein the non-transitory computer-readable medium stores computer readable instructions that, when executed by a processor, cause the processor to perform the method as defined in claim 1.

25. The apparatus according to claim 24, wherein the apparatus is a wearable device, a smartwatch or a patch.

\* \* \* \* \*

UNITED STATES PATENT AND TRADEMARK OFFICE
CERTIFICATE OF CORRECTION

PATENT NO. : 12,383,205 B2  
APPLICATION NO. : 17/684818  
DATED : August 12, 2025  
INVENTOR(S) : Olivatto Fioravanti et al.

Page 1 of 1

It is certified that error appears in the above-identified patent and that said Letters Patent is hereby corrected as shown below:

In the Claims

Column 24, Line 16:  
In Claim 6, delete "according" and insert -- according to --.

Column 25, Line 44:  
In Claim 16, delete "indicate;" and insert -- indicate: --.

Column 25, Line 46:  
In Claim 16, delete "position" and insert -- position; --.

Column 25, Line 50:  
In Claim 17, delete "trained." and insert -- trained, --.

Signed and Sealed this  
Fourth Day of November, 2025

John A. Squires  
*Director of the United States Patent and Trademark Office*